United States Patent
Fleming, III

(10) Patent No.: US 6,554,778 B1
(45) Date of Patent: Apr. 29, 2003

(54) BIOPSY DEVICE WITH REMOVABLE HANDLE

(75) Inventor: James A. Fleming, III, Buffalo Grove, IL (US)

(73) Assignee: Manan Medical Products, Inc., Wheeling, IL (US)

( * ) Notice: Subject to any disclaimer, the term of this patent is extended or adjusted under 35 U.S.C. 154(b) by 0 days.

(21) Appl. No.: 09/770,987

(22) Filed: Jan. 26, 2001

(51) Int. Cl.⁷ .............................................. A61B 10/00
(52) U.S. Cl. ........................................ 600/567; 606/167
(58) Field of Search .............................. 600/567, 562, 600/564, 565, 566; 606/167, 170

(56) References Cited

U.S. PATENT DOCUMENTS

| | | | |
|---|---|---|---|
| 3,844,291 A | 10/1974 | Moen | 128/354 |
| 3,949,747 A | 4/1976 | Hevesy | 128/2 B |
| 3,995,619 A * | 12/1976 | Glatzer | 128/305 |
| 4,256,119 A | 3/1981 | Gauthier | 128/754 |
| 4,262,676 A | 4/1981 | Jamshidi | 128/753 |
| 4,266,555 A | 5/1981 | Jamshidi | 128/753 |
| 4,356,828 A | 11/1982 | Jamshidi | 128/754 |
| 4,403,617 A | 9/1983 | Tretinyak | 128/754 |
| 4,513,754 A | 4/1985 | Lee | 128/753 |
| 4,609,370 A | 9/1986 | Morrison | 604/165 |
| 4,630,616 A * | 12/1986 | Tretinyak | 128/753 |
| 4,651,752 A | 3/1987 | Fuerst | 128/754 |
| 4,655,226 A * | 4/1987 | Lee | 128/754 |
| 4,785,826 A | 11/1988 | Ward | 128/754 |
| 4,793,363 A | 12/1988 | Ausherman et al. | 128/754 |
| 4,838,282 A * | 6/1989 | Strasser et al. | 128/754 |
| D303,009 S | 8/1989 | Strasser et al. | D24/24 |
| 4,922,602 A | 5/1990 | Mehl | 29/460 |
| 5,036,860 A | 8/1991 | Leigh et al. | 128/754 |
| 5,074,311 A | 12/1991 | Hasson | 128/754 |
| 5,090,419 A | 2/1992 | Palestrant | 128/754 |
| 5,127,419 A | 7/1992 | Kaldany | 128/754 |

(List continued on next page.)

FOREIGN PATENT DOCUMENTS

DE      255 278 A1    3/1988       A61B/10/00

*Primary Examiner*—Henry C. Yuen
*Assistant Examiner*—Frederick Nicolas
(74) *Attorney, Agent, or Firm*—Greenberg Traurig, P.C.

(57) ABSTRACT

A biopsy device includes an outer cannula, an inner rod, a sheath operably associated with the outer cannula, a handle assembly removably attachable to the sheath, and a release member for releasably attaching the handle assembly to the sheath. In one embodiment, a locking element associated with the sheath comprises a pair of notches located on either side of the sheath, and a locking element associated with the handle assembly comprises a pair of slots in communication with an opening within the handle assembly. The release member comprises a rotatable collar located in a channel on the handle assembly. When the release member is rotated from a first position to a second position, a portion thereof protrudes through the slots into the notches on the sheath, thereby locking the sheath in place.

15 Claims, 10 Drawing Sheets

U.S. PATENT DOCUMENTS

| | | | | |
|---|---|---|---|---|
| 5,148,813 | A | 9/1992 | Bucalo | 128/754 |
| 5,172,700 | A | 12/1992 | Becini et al. | 128/751 |
| 5,186,197 | A | 2/1993 | Lavine | 135/25.4 |
| 5,257,632 | A | 11/1993 | Turkel et al. | 128/754 |
| 5,286,255 | A | 2/1994 | Weber | 604/22 |
| 5,318,589 | A | 6/1994 | Lichtman | 606/205 |
| 5,331,972 | A | 7/1994 | Wadhwani et al. | 128/754 |
| 5,333,619 | A | 8/1994 | Burgio | 128/754 |
| 5,357,974 | A | 10/1994 | Baldridge | 128/754 |
| 5,385,151 | A | 1/1995 | Scarfone et al. | 128/754 |
| 5,429,138 | A | 7/1995 | Jamshidi | 128/753 |
| 5,462,062 | A | 10/1995 | Rubinstein et al. | 128/754 |
| 5,476,102 | A | 12/1995 | Como et al. | 128/754 |
| 5,522,398 | A | 6/1996 | Goldenberg et al. | 128/754 |
| 5,526,821 | A | 6/1996 | Jamshidi | 128/753 |
| 5,538,009 | A | 7/1996 | Byrne et al. | 128/754 |
| 5,595,186 | A | 1/1997 | Rubenstein et al. | 128/754 |
| 5,634,473 | A * | 6/1997 | Goldenberg et al. | 128/754 |
| 5,752,923 | A | 5/1998 | Terwilliger | 600/562 |
| 5,758,655 | A | 6/1998 | Rodriguez et al. | 128/749 |
| 5,807,275 | A | 9/1998 | Jamshidi | 600/567 |
| 5,807,277 | A | 9/1998 | Swaim | 600/567 |
| 5,833,662 | A * | 11/1998 | Stevens | 609/167 |
| 5,843,001 | A | 12/1998 | Goldenberg | 600/567 |
| 5,871,471 | A | 2/1999 | Ryan et al. | 604/167 |
| 5,910,121 | A * | 6/1999 | Paolo et al. | 600/562 |
| 5,948,008 | A | 9/1999 | Daikuzono | 607/89 |
| 5,971,939 | A * | 10/1999 | DeSantis et al. | 600/562 |
| 6,015,391 | A | 1/2000 | Rishton et al. | 600/587 |
| 6,033,369 | A | 3/2000 | Goldenberg | 600/567 |
| 6,221,029 | B1 | 4/2001 | Mathis et al. | 600/564 |
| 6,302,852 | B1 * | 10/2001 | Fleming, III et al. | 600/567 |
| 6,312,394 | B1 * | 11/2001 | Fleming, III | 600/567 |
| 6,340,351 | B1 * | 1/2002 | Goldenberg | 600/567 |

* cited by examiner

BIOPSY DEVICE WITH REMOVABLE HANDLE

BACKGROUND OF THE INVENTION

1. Field of the Invention

The present invention relates in general to biopsy devices and, more particularly, to a biopsy device with a removable handle assembly.

2. Background Art

Biopsy devices have been known in the art for many years. In particular, many such biopsy devices have included a hollow outer cannula with some form of inner rod slidable within the outer cannula. The outer cannula conventionally consists of a proximal end, a distal end, and some form of a handle associated with the proximal end. The inner rod may typically take several different forms, including a sharpened stylet for insertion of the biopsy device into a patient, an inner cannula for sampling tissue, and/or an ejector rod for forcing the sample out of the outer cannula. The inner rod also typically includes a second or connection handle which may be secured to the handle portion of the outer cannula.

Such devices typically provide for the securable joining together of the outer cannula and inner rod handles when the inner rod is inserted within the outer cannula. Once the entire assembly is inserted within a patient, the inner rod is typically removed by separating the outer cannula and inner rod handles, and removing the inner rod by means of the inner rod handle. This type of structure is disclosed by Baldridge, U.S. Pat. No. 5,357,974, Tretinvak, U.S. Pat. No. 4,403,617, Tretinvak, U.S. Pat. No. 4,630,616, Lee, U.S. Pat. No. 4,655,266, and Strasser, et al., U.S. Pat. No. 4,838,282, among others.

Many of these types of devices require rotation of one of the handles themselves to unlock and separate the handles from one another, resulting in a change of orientation of the handles with respect to one another while the device is within the patient. This change in orientation of the handles, however, can often cause a corresponding change in the orientation of the inner rod with respect to the outer cannula, which can be undesirable to the user. Likewise, the manipulations of the overall device while in use can inadvertently separate the cannula handle from the rod handle, unlocking the device and causing the aligned tips of the cannula and rod to become misaligned. Other such devices contain a locknut securing device positioned directly atop the inner rod, which must be repeatedly rotated in order to remove the inner rod, thereby allowing the user to directly remove the rod itself from the interior of the cannula.

One application in which such devices are used is to repair crushed vertebrae. Typically, the cannula and rod portions of the biopsy device are inserted within the patient in order to locate the proper vertebra. After the cannula has been positioned within a vertebra, then an imaging device, such as an x-ray machine, is used to view the location of the cannula tip to determine whether it is positioned properly. If the cannula is not in the desired position, then the position of the biopsy device is adjusted as needed. Once it is determined that the cannula is positioned properly, then the inner rod is removed, and a form of cement or other binding element is injected into the vertebra through the cannula in order to reexpand the crushed vertebra. The devices in the prior art, however, present a particular disadvantage for this type of application. Once the user has removed the inner rod, along with its corresponding handle, the outer cannula handle remains in place, providing an undesired impediment to the imaging process.

It is therefore desired to provide a biopsy device with a separate handle assembly which is capable of being removed after the device is inserted into a patient, leaving the outer cannula and inner rod in place in the desired location, thereby eliminating the impediment to the imaging process presented by the presence of the outer cannula handle, as described above.

It is further desired to provide a biopsy device which allows the user to readily unlock and remove the handle assembly without affecting the orientation of the outer cannula and the inner rod with respect to one another, in order to prevent an undesired corresponding change in orientation of the distal ends of each.

Another object of the invention is to provide a biopsy device having a threaded region for the connection of external devices to the outer cannula, thereby allowing the outer cannula to be used with any number of medical devices requiring access to interior regions of the body.

It is also an object of the invention to provide a biopsy device in which the handle assembly may be resterilized after use and reused, resulting in significant cost savings over similar devices with attached handles which are disposed along with the rest of the device after use.

These and other objects of the present invention will become apparent in light of the present specification, claims, and drawings.

SUMMARY OF THE INVENTION

The present invention is directed to a biopsy device having a removable handle for alternatively attaching and removing a handle assembly while the cannula portion of the device is inserted into a patient, without affecting the orientation of the cannula portion of the device within the patient. The biopsy device comprises an outer cannula having a proximal end, a distal end, and a substantially hollow cross-section between the proximal and distal ends; an inner rod capable of being telescopically inserted into and retracted from the outer cannula and having a proximal end and a distal end; a sheath operably associated with and surrounding at least a portion of the outer cannula, and comprising a locking element; a handle assembly removably attachable to the sheath comprising a locking element and an opening for receiving at least a portion of the sheath; and a release member for releasing the handle assembly from attachment to the sheath by interacting with the locking elements associated with the sheath and the handle assembly. Further, the sheath may be at least partially inserted within the opening in the handle assembly and attached thereto, thereby retainably, yet releasably, locking the handle assembly to the outer cannula and the inner rod.

In another embodiment of the invention, the release member is a release element which is capable of toggling by the user between at least two positions in order to alternatively lock and release the handle assembly to the sheath.

In a further embodiment, the locking element associated with the sheath comprises at least one slot on the sheath which is capable of interacting with the release member to prevent separation of the sheath and the handle assembly.

In a still further embodiment, the locking element associated with the handle assembly comprises at least one aperture in the handle assembly which is capable of interacting with the release member to prevent separation of the sheath and the handle assembly.

In a yet further embodiment, the release member comprises a rotatable collar associated with at least one of the sheath and the handle assembly, and which is capable of being rotated at least partially about the sheath and the handle assembly when the two are joined together. The rotatable collar has at least two stationary positions, so that when the collar is in one position, a portion of the collar interacts with both of the locking elements associated with the sheath and the handle assembly to prevent separation of the sheath and the handle assembly. When the collar is in the other position, it avoids interaction with both of the locking elements, thereby permitting separation of the sheath and handle assembly from one another.

In an alternative embodiment, the release member comprises a slide member associated with at least one of the sheath and the handle assembly, and which is capable of lateral movement relative to the sheath and the handle assembly when the two are joined together. The slide member has at least two stationary positions, so that when the slide member is in one position, a portion of the slide member interacts with both of the locking elements associated with the sheath and the handle assembly to prevent separation of the sheath and the handle assembly. When the slide member is in the other position, it avoids interaction with both of the locking elements, thereby permitting separation of the sheath and handle assembly from one another.

In another embodiment of the invention, the opening in the handle assembly for receipt of the sheath is asymmetrical about at least one axis substantially perpendicular to the longitudinal axis of the opening.

In a further embodiment, at least a portion of the sheath has an asymmetrical cross-section substantially similar to that of the asymmetrical opening in the handle assembly, so as to be insertable into the handle assembly only when the sheath and the handle assembly are aligned in one particular orientation. This ensures that the outer cannula and the inner rod will be aligned in the same particular orientation relative to the handle assembly when the sheath and the handle assembly are locked together.

In still another embodiment of the invention, at least a portion of the outer surface of the sheath is threaded to enable the attachment of a comparably threaded component of a separate conduit for attachment to the outer cannula after the handle assembly is removed from the sheath.

An additional embodiment of the invention further includes an attachment member for securably attaching the inner rod within the outer cannula.

In a further embodiment, the attachment member comprises at least one prong associated with the inner rod for engaging with the sheath to securably attach the inner rod within the outer cannula.

Yet another embodiment includes a locking indicia for readily indicating whether the sheath and the handle assembly are in a locked or an unlocked orientation, relative to one another.

In alternative embodiments of the invention, the inner rod may comprise at least one of an inner cannula, a stylet, an obturator and an ejector rod.

BRIEF DESCRIPTION OF THE DRAWINGS

FIG. 1b is an exploded perspective view of the biopsy device shown in FIG. 1a.

FIG. 2 is a front elevational view of the biopsy device shown in FIG. 1a.

FIG. 3 is a side elevational view of the biopsy device shown in FIG. 1a.

FIG. 6b is a front elevational view of the lower portion of the handle body shown in FIG. 6a.

FIG. 6c is a side elevational view of the lower portion of the handle body shown in FIG. 6a.

FIG. 6d is a top plan view of the lower portion of the handle body shown in FIG. 6a.

FIG. 7a is a perspective view of the sheath portion of the biopsy device shown in FIG. 1a.

FIG. 7b is a front elevational view of the sheath portion shown in FIG. 7a.

FIG. 7c is a side elevational view of the sheath portion shown in FIG. 7a.

FIG. 7d is a top plan view of the sheath portion shown in FIG. 7a.

FIG. 8a is a perspective view of the release member of the biopsy device shown in FIG. 1a.

FIG. 8b is a front elevational view of the release member shown in FIG. 8a.

FIG. 8c is a top plan view of the release member shown in FIG. 8a.

FIG. 8d is a side elevational view of the release member shown in FIG. 8a.

FIG. 9b is a front elevational view of the lower portion of the handle body shown in FIG. 9a.

FIG. 9c is a side elevational view of the lower portion of the handle body shown in FIG. 9a.

FIG. 9d is a top plan view of the lower portion of the handle body shown in FIG. 9a.

FIG. 10a is a perspective view of the sheath portion of the embodiment shown in FIG. 9a.

FIG. 10b is a front elevational view of the sheath portion shown in FIG. 10a.

FIG. 10c is a side elevational view of the sheath portion shown in FIG. 10a.

FIG. 10d is a top plan view of the sheath portion shown in FIG. 10a.

FIG. 11a is a perspective view of the release member of the embodiment shown in FIG. 9a.

FIG. 11b is a front elevational view of the release member shown in FIG. 10a.

FIG. 11c is a top plan view of the release member shown in FIG. 10a.

FIG. 11d is a side elevational view of the release member shown in FIG. 10a.

DETAILED DESCRIPTION OF THE INVENTION

Figure 1A:
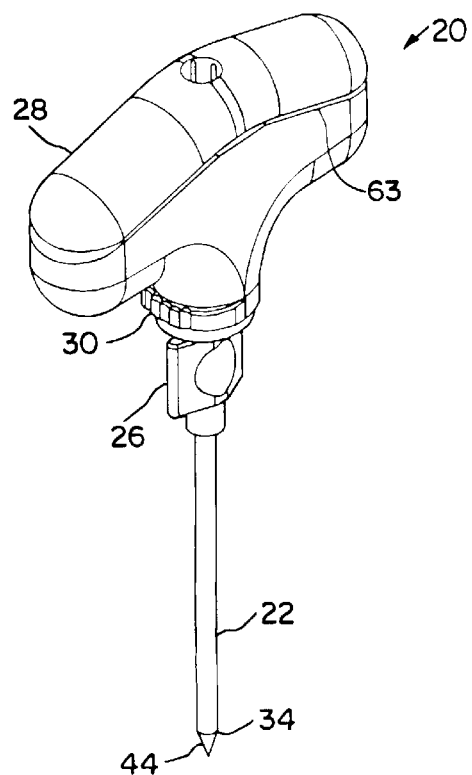
FIG. 1a is a perspective view of the biopsy device according to the present invention, showing the handle assembly portion of the device lockably attached to the sheath portion.
Figure 2:
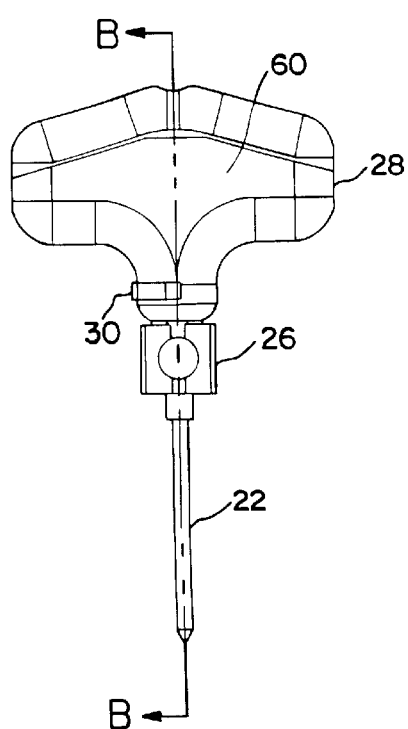
Figure 3:
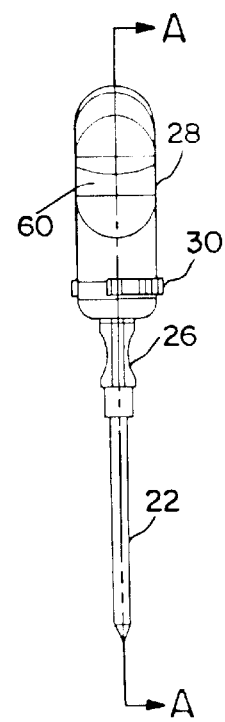
Figure 1B:
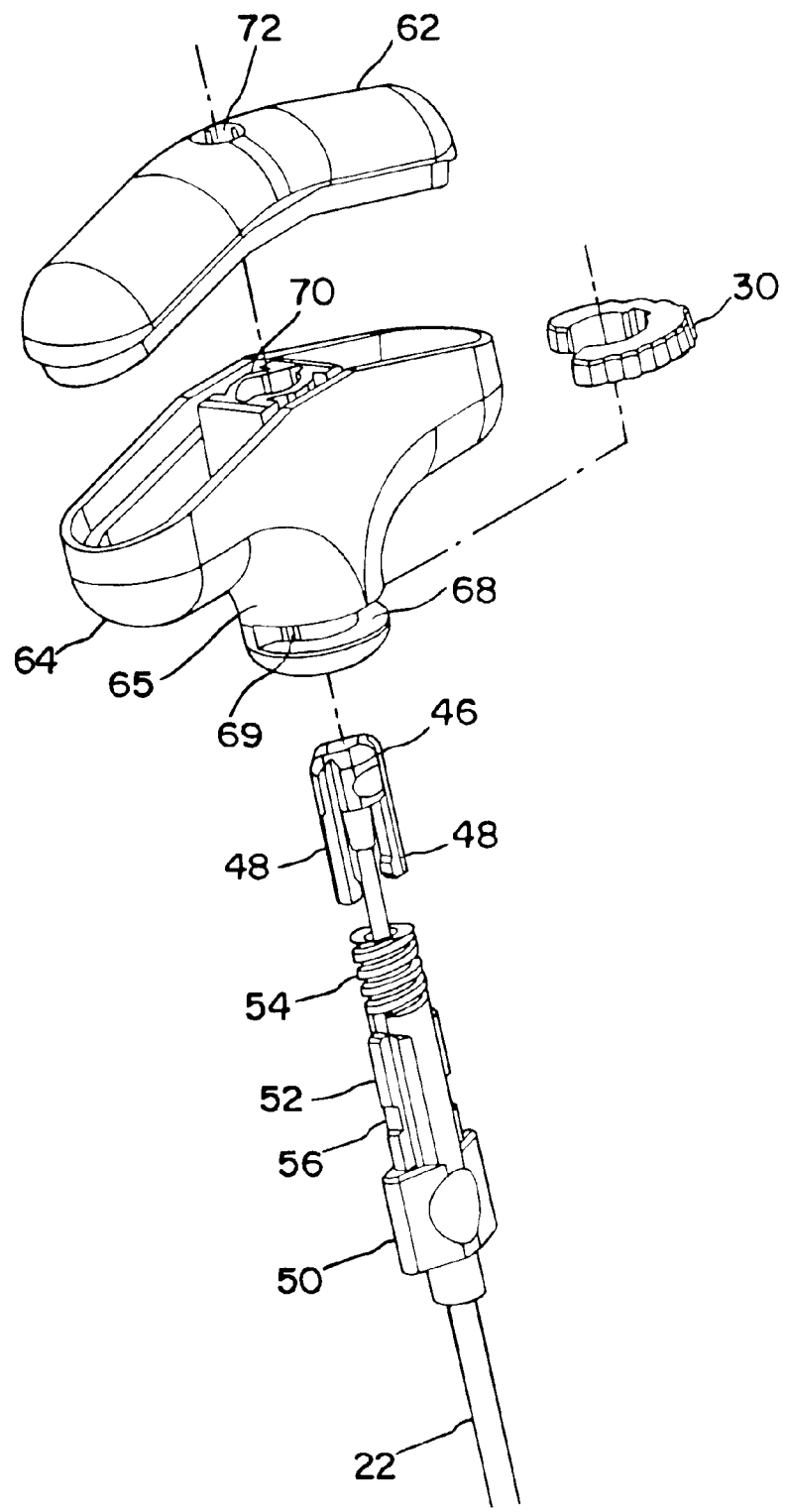

While this invention is susceptible of embodiment in many different forms, there is shown in the drawings, and will herein be described in detail, several specific embodiments, with the understanding that the present disclosure can be considered as an exemplification of the principals of the invention and is not intended to limit the invention to the embodiments illustrated.

Biopsy device 20 is shown in FIGS. 1–8 as comprising outer cannula 22, inner rod 24, sheath 26, handle assembly 28, and release member 30. Outer cannula 22 comprises a cylindrical tube, preferably fashioned from stainless steel or other metal, having distal end 34. While outer cannula 22 is shown here as having a flush distal end 34, distal end 34 may also comprise a saddle point or other configuration conducive to cutting through human tissue. Moreover, distal end 34 may also include an inner tapered portion to facilitate retrieval of tissue, such as disclosed in Mittermeier, U.S. Pat. No. 6,063,037.

Figure 4:
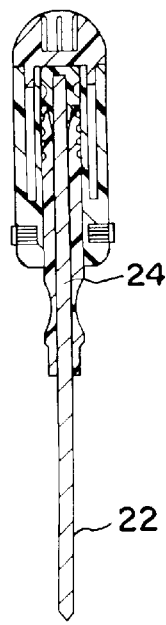
FIG. 4 is an elevated cross-sectional view of the biopsy device shown in FIG. 1a taken along lines B—B of FIG. 2, and looking in the direction of the arrows.
Figure 5:
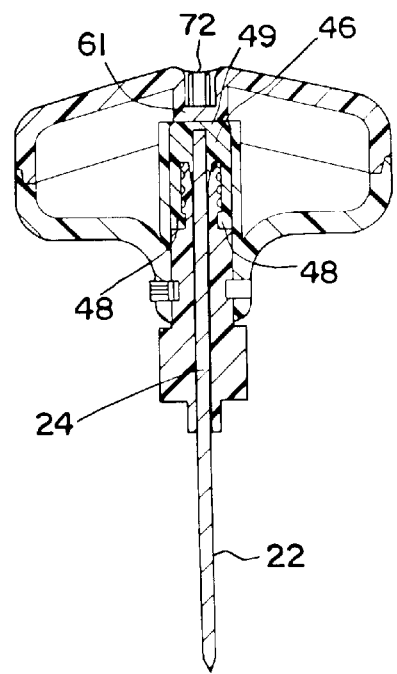
FIG. 5 is an elevated cross-sectional view of the biopsy device shown in FIG. 1a taken along lines A—A of FIG. 3, and looking in the direction of the arrows.
Figure 6A:
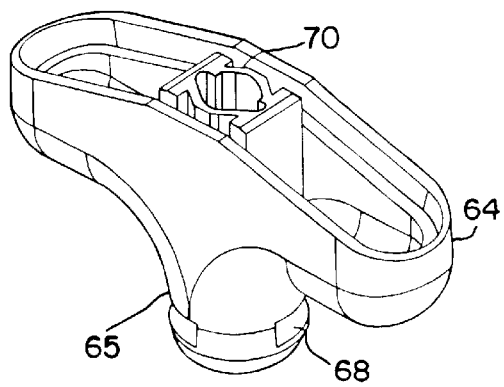
FIG. 6a is a perspective view of the lower portion of the handle body of the biopsy device shown in FIG. 1a, showing the sheath housing within the handle body.
Figure 6C:
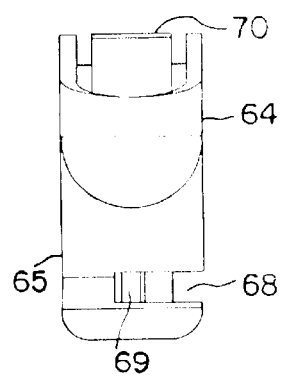
Figure 6B:
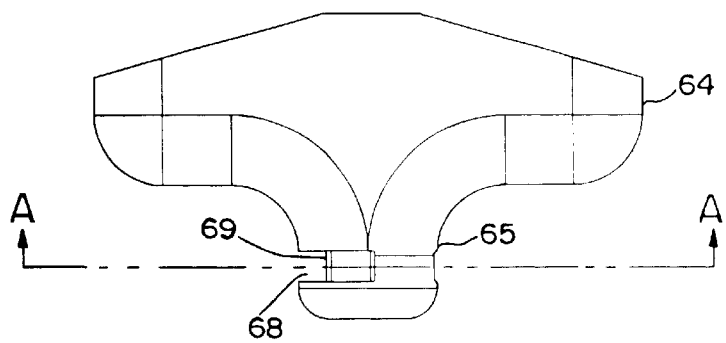
Figure 6D:
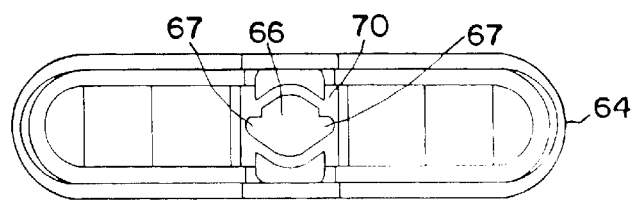
Figure 6E:
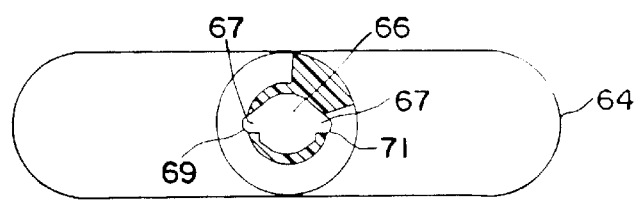
FIG. 6e is a cross-sectional bottom plan view of the lower portion of the handle body shown in FIG. 6a taken along lines A—A of FIG. 6b, and looking in the direction of the arrows.
Figure 7A:
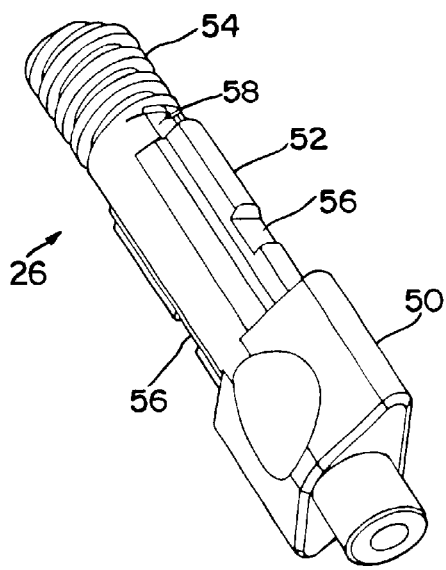
Figure 7C:
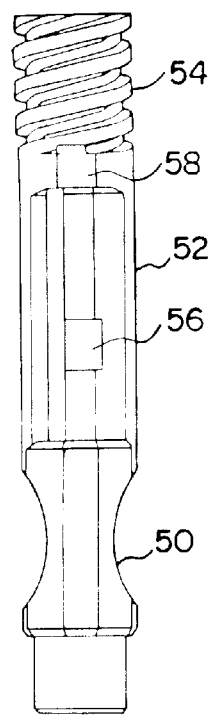
Figure 7B:
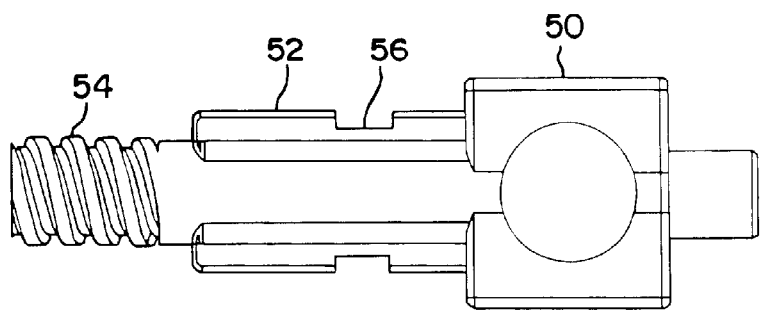
Figure 7D:
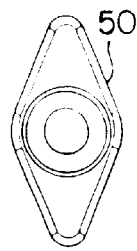
Figure 8A:
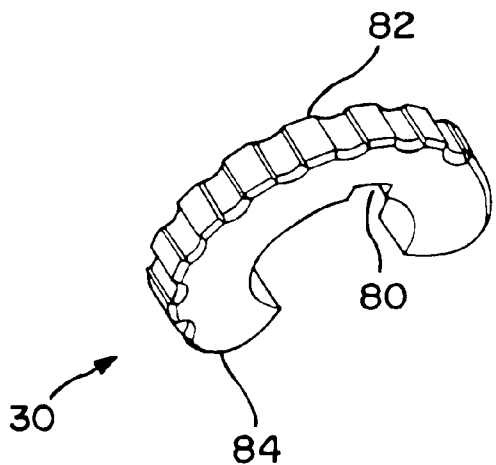
Figure 8C:
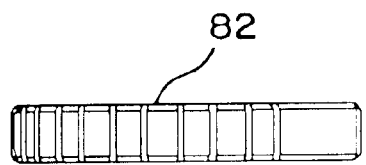
Figure 8B:
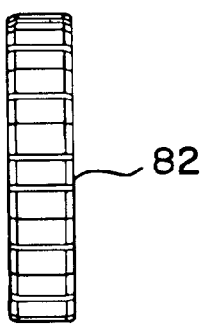
Figure 8D:
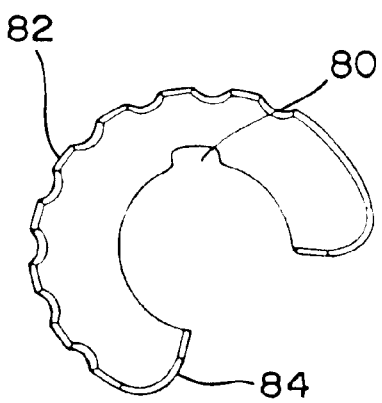

Inner rod 24 is shown in FIGS. 4 and 5 as comprising a cylindrical rod contained within outer cannula 22, having distal end 44, and an attachment member 46. Attachment member 46 includes prongs 48, which are preferably flexible and biased inward, for attachment of inner rod 24 to sheath 26, and proximal end 49. Attachment member 46 typically has the same cross-sectional shape as barrel portion 52 of sheath 26, so that inner rod 24 and outer cannula 22 may be joined to handle assembly 28, as described below. While inner rod 24 is shown here as being shorter than outer cannula 22 and having a blunt distal end 44, typically inner rod 24 will be longer than outer cannula 22 and will have a sharpened stylet or obturator which protrudes from outer cannula 22 for cutting through human tissue. Additionally, inner rod 24 may also comprise a hollow inner cannula for sampling tissue, an ejector rod for forcing tissue from outer cannula 22, as well as other types of inner rods commonly used with such biopsy devices known by those of ordinary skill in the art having the present disclosure before them.

Sheath 26 is shown in FIGS. 7a–7d as comprising base portion 50, barrel portion 52 and thread 54. Sheath 26 surrounds outer cannula 22, and is preferably constructed from plastic or similar material. Sheath 26 progressively decreases in width from bottom to top, with base portion 50 having the largest width, and barrel portion 52 and thread 54 being successively smaller in width. Barrel portion 52 includes locking elements thereon, namely notches 56 on either side thereof for interacting with release member 30, as described below. Thread 54 includes notches 58 which facilitate the connection of inner rod 24 and outer cannula 22. When inner rod 24 is inserted within outer cannula 22, prongs 48 encounter thread 54 and are bent slightly outward. When prongs 48 have passed over thread 54, they return to their unbent position, coming to rest within notches 58. Because prongs 48 are biased inward, they are therefore held in place in notches 58, thereby securing inner rod 24 in place relative to outer cannula 22. Because prongs 48 are flexible, however, inner rod 24 can be easily separated from outer cannula 22 by pulling on attachment member 46, which causes prongs 48 to encounter thread 54 and bend outward.

Thread 54 is also adapted for the connection of external medical devices to outer cannula 22 by means of a threaded connector. These may include devices for suction, devices for injecting matter into a body cavity, endoscopic devices for examining the interior of the body, and any other devices which would be obvious to one of ordinary skill in the art. This feature allows the user of the biopsy device to accomplish multiple tasks in a particular region of the body without having to insert a separate needle for each task.

Handle assembly 28 is shown in FIGS. 1a, 1b, 2, 3, 5, and 6a–6e as comprising handle body 60, opening 66, channel 68, sheath housing 70, and insert hole 72. Handle body 60 comprises upper portion 62, lower portion 64, and neck portion 65. In this embodiment, upper portion 62 and lower portion 64 are separate pieces, joining together at seam 63. However, this separation of handle body 60 into two components is solely to facilitate the molding of handle body 60, and is not necessary to practice the invention. Upper portion 62 further includes stop 61, which constitutes an inward projection that is aligned with the proximal end of sheath housing 70, to restrain the position of proximal end 49 of attachment member 46 and ensure orientation of inner rod 24 with outer cannula 22. Opening 66 leads into sheath housing 70, which extends vertically through the interior of handle body 60, and which includes side portions 67. Sheath housing 70 has the same cross-section as barrel portion 52 of sheath 26, and holds barrel portion 52 in place when sheath 26 and handle assembly 28 are joined together. Insert hole 72 is adapted for the placement of a rubber insert (not shown) to absorb some of the force generated by the use of a hammer or similar device in connection with the insertion of biopsy device 20 into a patient, so as to minimize the amount of noise generated by the application of such force.

In the present embodiment, opening 66 has an oblong shape which is asymmetrical about the longer axis of handle assembly 28, and which corresponds to the cross-sectional shape of barrel portion 52 of sheath 26. As a result, opening 66 will receive barrel portion 52 only when sheath 26 and handle assembly 28 are aligned in the correct orientation. This design feature ensures that distal end 34 of outer cannula 22 and distal end 44 of inner rod 24 are aligned in a desired orientation relative to one another when sheath 26 and handle assembly 28 are joined together, and that sheath 26 and handle assembly 28 cannot be joined in any other orientation.

Channel 68 comprises a shallow channel on the outside of neck portion 65 which extends approximately three-quarters of the way around neck portion 65. Channel 68 includes locking elements, namely slots 69 and 71, which are located opposite from one another and open into side portions 67 of sheath housing 70. When handle assembly 28 is viewed from the front, as in FIG. 6b, slots 69 and 71 are located within channel 68 on the left and right-hand sides of neck 65, respectively. Channel 68 begins at slot 71, and extends counterclockwise approximately one-quarter revolution past slot 69, terminating at the front of neck 65.

Release member 30 is shown in FIGS. 8a–8d as a substantially flat, semicircular member having an aperture diameter slightly larger than the inner diameter of channel 68, and which includes notch 80 and dimpled or knurled portion 82, which provides a gripping surface to facilitate rotation of release member 30 by the user. Release member 30 is adapted to fit within channel 68 and has an outer circumference extending slightly less than three-quarters around neck portion 65, so that release member 30 is able to be manipulated and rotate within channel 68 about a small angular displacement on the order of one-eighth of one rotation. This effectively allows for release member 30 to be toggled between two positions, which correspond to the locked and unlocked orientation of handle assembly 28. When release member 30 is rotated counterclockwise as far as possible, no portions of release member 30 protrude through slots 69 and 71, as a result of which side portions 67 of sheath housing 70 are unobstructed. This owes to the fact that, on the left-hand side of channel 68, notch 80 is aligned with slot 69, and on the right-hand side of channel 68, the end 84 of release member 30 is located slightly counter-clockwise of slot 71. This position corresponds to the unlocked orientation of biopsy device 20, as described below. Alternatively, when release member 30 is rotated clockwise as far as possible, notch 80 is no longer aligned with slot 69, thereby causing a portion of release member 30 to protrude through slot 69 and obstruct one side portion 67 of sheath housing 70. Additionally, the end 84 of release member 30 now protrudes through slot 71, obstructing the other side portion 67 of sheath housing 70. This position of release member 30 corresponds to the locked orientation of biopsy device 20.

In order to join handle assembly 28 to sheath 26, and thereby to outer cannula 22 and inner rod 24, sheath 26 must first be inserted into opening 66 in handle assembly 28. In order to do so, release member 30 must be in the unlocked position, in which notch 80 is aligned with slot 69, in order to permit insertion of sheath 26. If release member 30 is in the locked position, then side portions 67 will be obstructed by release member 30 as described above, thereby preventing full insertion of sheath 26. Opening 66 will accommodate sheath 26 with or without inner rod 24 attached, owing to the fact that attachment member 46 of inner rod 24 and barrel portion 52 of sheath 26 have substantially identical cross-sections. When inserted, sheath 26 passes through opening 66 into sheath housing 70, which is of a sufficient length to accommodate both barrel portion 52 and thread 54. When barrel portion 52 is fully inserted into sheath housing 70, base portion 50 will abut the bottom of neck portion 65 of handle assembly 28, and notches 56 on barrel portion 52 will be aligned with slots 69 and 71.

Once sheath 26 has been fully inserted into sheath housing 70, the user may then lock handle assembly 28 to sheath 26 by rotating release member 30 clockwise. As release member 30 is rotated from its unlocked position to its locked position, sheath 26 is fixed in place within sheath housing 70, due to the fact that the portions of release member 30 which protrude through slots 69 and 71 into notches 56 prevent sheath 26 from moving. Because sheath 26 is fixed in place, prongs 48 on inner rod attachment member 46 are held in place by the walls of sheath housing 70, thereby ensuring that outer cannula 22 and inner rod 24 remain fixed in place relative to one another while sheath 26 and handle assembly 28 are locked together. Additionally, sheath 26 and handle assembly 28 are maintained in axial alignment, relative to one another, by proximal end 49 of attachment member 46, which abuts stop 61 on upper portion 62 of handle assembly 28, as shown in FIG. 5, thereby preventing inner rod (stylet) 24 from moving longitudinally within outer cannula 22. This likewise ensures a matched grind between the distal ends of cannula 22 and rod 24. Therefore, the user of biopsy device 20 can use a large amount of force, if necessary, to manipulate biopsy device 20 in order to penetrate tissue and/or bone, without undesired movement of the distal ends of outer cannula 22 and inner rod 24 relative to one another.

One application for which biopsy device 20 is particularly well-suited is that of repairing crushed vertebrae. In this type of application, inner rod 24 typically comprises a sharpened stylet, which is used to penetrate tissue in order to reach the vertebrae. Once outer cannula 22 and inner rod 24 have been positioned within the desired vertebra, handle assembly 28 is removed from sheath 26 by means of release member 30, as described above, in order to facilitate use of an imaging device to view the vertebral region to determine whether the distal end 34 of outer cannula 22 is in the desired location. If it is determined that outer cannula 22 and inner rod 24 are not positioned as desired, then handle assembly 28 may be reattached to sheath 26 in order to reposition biopsy device 20. Once outer cannula 22 and inner rod 24 have been placed in the desired position, then inner rod 24 may then be removed from outer cannula 22 by means of attachment member 46. Cement or other desired material may then be injected into the vertebra through outer cannula 22 by means of attachment of an external component to thread 54 in order to inflate the crushed vertebra. When the procedure is complete, handle assembly 28 may then be reattached to sheath 26 in order to remove biopsy device 20 from the patient.

Another embodiment of the invention is shown in FIGS. 9–11. In this embodiment, the outer cannula and inner rod portions (not shown) are substantially identical to those in the embodiment of FIGS. 1–8. Lower portion 164 of handle assembly 128 is shown in FIGS. 9a–9h as comprising opening 166, sheath housing 170, slots 172 and 174, and indicia 176. Upper portion of handle assembly (not shown) is identical to upper portion 62 of the previous embodiment. As in the previous embodiment, the separation of handle assembly 128 into multiple parts is not necessary to practice the invention. Indicia 176 preferably comprises a visual indicator which indicates to the user whether handle assembly 128 is in the locked or unlocked orientation, which in this embodiment takes the form of two lines, with the letters "L" (for locked) and "U" for unlocked written above them.

Sheath 126 is shown in FIGS. 10a–10d as comprising base portion 150, barrel portion 152, and thread 154. Barrel portion 152 includes notch 156, which in this embodiment comprises a single notch located on the front side of barrel portion 152, and thread 154 includes notches 158 for receipt of the prong portions of the inner rod, as in the previous embodiment.

Release member 130 is shown in FIGS. 11a–11e as comprising slide portion 180, projection 182, and connection member 184. Release member 130 attaches to the front of handle assembly 128 such that release member 130 reciprocates along the front surface of handle assembly 128. Slide portion 180 comprises a rectangular member with rounded ends which is flat on one side and has a raised midsection on the other side to facilitate manipulation by hand. Connection member 184 comprises a pair of flanges 186 protruding from the flat side of slide portion 180. The flanges protrude through slot 174 on handle assembly 128, and are restrained from being removed due to the fact that connection member 184 is wider than slot 174, which serves to fixedly attach release member 130 to handle assembly 128. Projection 182 comprises a parallelepiped-shaped structure with one corner cut off, which protrudes from the flat side of slide portion 180.

Sheath 126 and handle assembly 128 are alternatively locked and unlocked by sliding release member 130 from its locked position to its unlocked position, and vice versa. Release member 130 is in the unlocked position when it is in its rightmost position. In this position, notch 156 on sheath 126 is aligned with the cut-out portion of projection 182, as a result of which sheath 126 and handle assembly 128 may be easily separated merely by pulling them apart. When release member 130 is moved to its leftmost position, then projection 182 correspondingly translates to the left, causing a portion of projection 182 to protrude into notch 156. When one attempts to remove handle assembly 128 from sheath 126, projection 182 will exert a force on the side of notch 156, preventing removal of handle assembly 128 from sheath 126. As a result, the leftmost position of release member 130 corresponds to the locked position, due to the fact that sheath 126 and handle assembly 128 are securely attached to one another, while the rightmost position of release member 130 corresponds to the unlocked position.

Figure 9A:
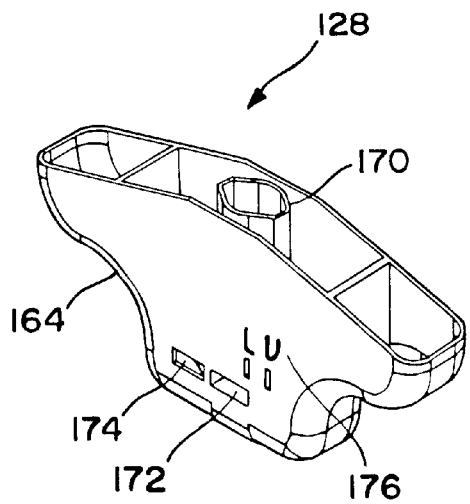
FIG. 9a is a perspective view of the lower portion of the handle body of the biopsy device according to another embodiment of the present invention.
Figure 9G:
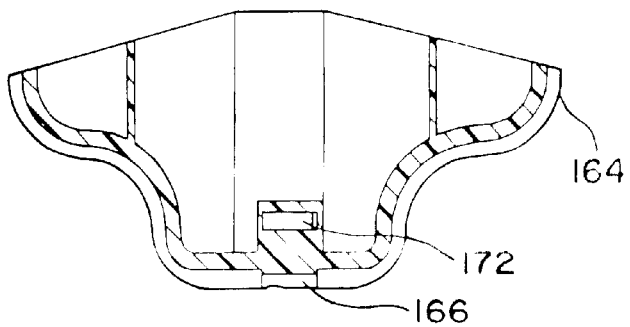
FIG. 9g is a cross-sectional elevated front view of the lower portion of the handle body shown in FIG. 9a taken along lines C—C of FIG. 9b, and looking in the direction of the arrows.
Figure 9E:
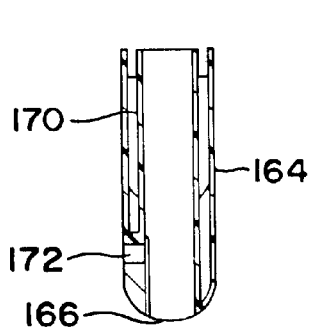
FIG. 9e is a cross-sectional elevated side view of the lower portion of the handle body shown in FIG. 9a taken along lines A—A of FIG. 9b, and looking in the direction of the arrows.
Figure 9C:
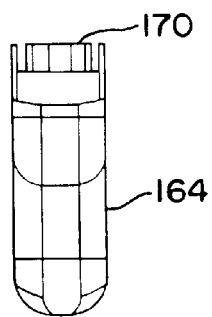
Figure 9F:
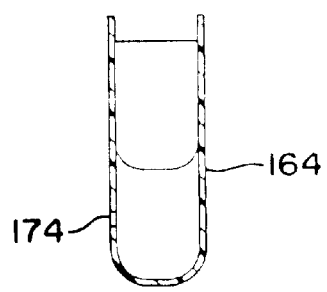
FIG. 9f is a cross-sectional elevated side view of the lower portion of the handle body shown in FIG. 9a taken along lines B—B of FIG. 9b, and looking in the direction of the arrows.
Figure 9H:
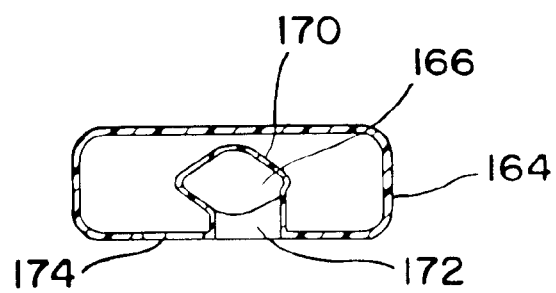
FIG. 9h is a cross-sectional top plan view of the lower portion of the handle body shown in FIG. 9a taken along lines D—D of FIG. 9b, and looking in the direction of the arrows.
Figure 9D:
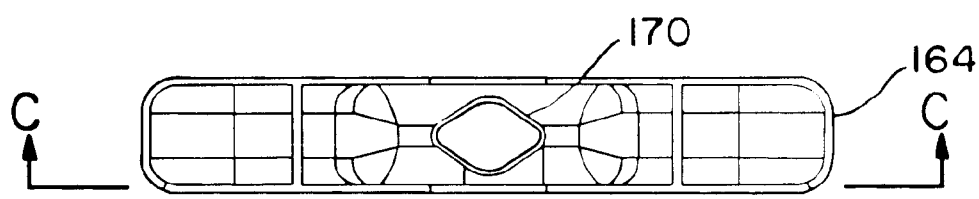
Figure 9B:
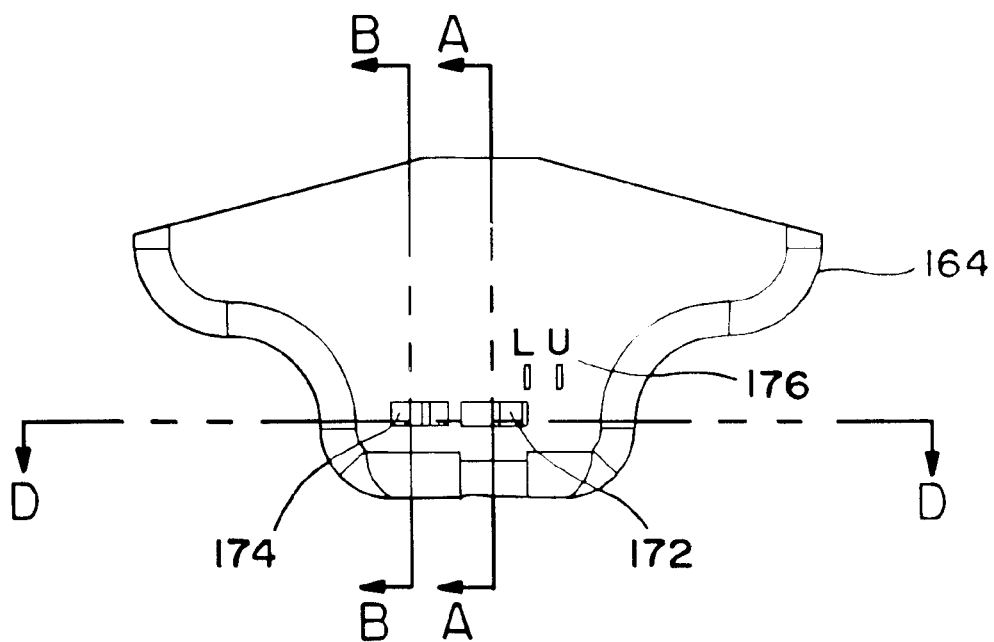
Figure 10A:
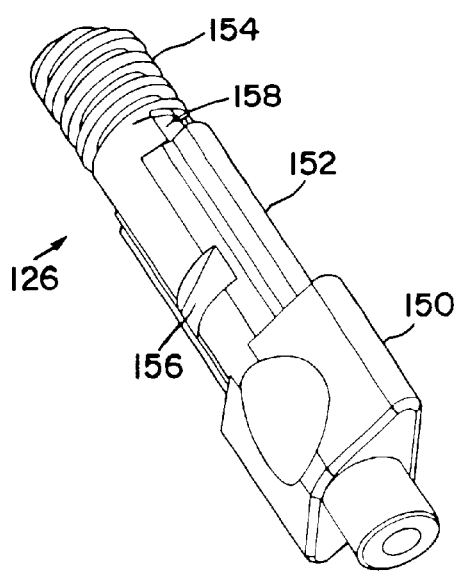
Figure 10C:
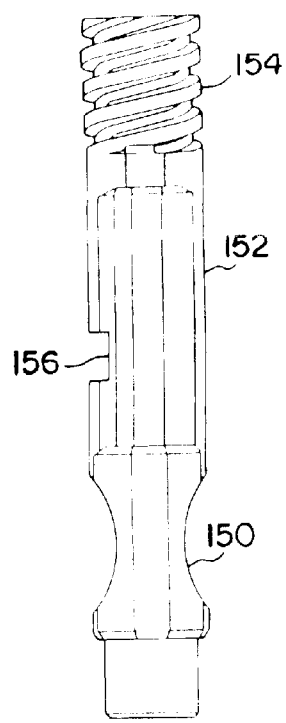
Figure 10B:
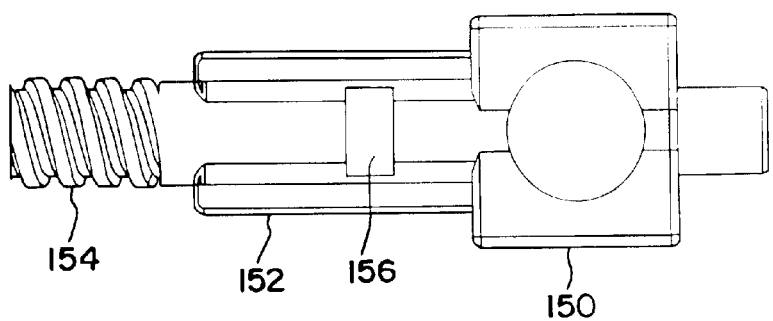
Figure 10D:
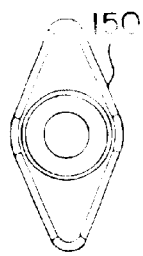
Figure 11A:
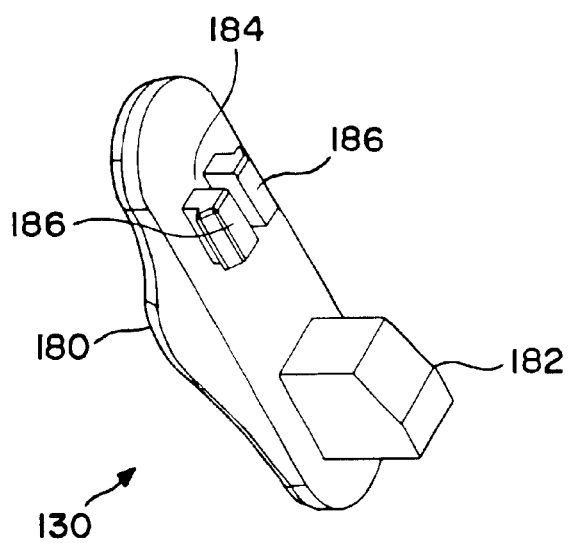
Figure 11C:
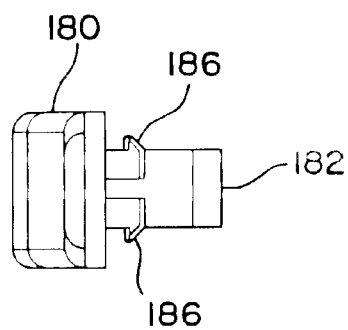
Figure 11B:
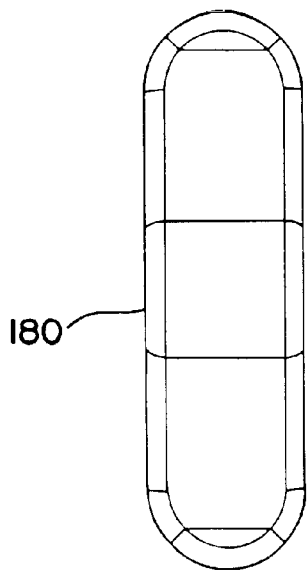
Figure 11D:
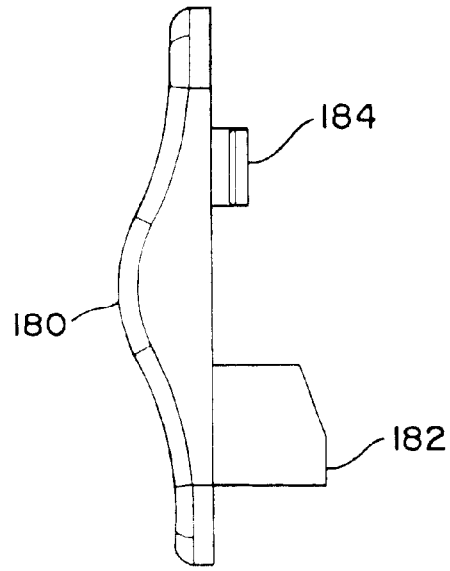

Further, release member 130 interacts with indicia 176 to indicate whether the release member is in the locked or unlocked position, as shown in FIGS. 9a and 9b. When release member 130 is in its rightmost, or unlocked, position, then the right end of release member is aligned with the right mark of indicia 176, above which is written the letter "U", for "unlocked". Similarly, when release member 130 is in its leftmost, or locked position, the right end of release member 130 is aligned with the left mark of indicia 176, above which is written the letter "L", for "locked". Thus, the user will be able to tell whether the release member 130 is in its locked or unlocked position merely by glancing at handle assembly 128.

The foregoing description and drawings are merely to explain and illustrate the invention, and the invention is not limited thereto except insofar as the independent claims are so limited, as those skilled in the art with the present disclosure before them will be able to make modifications and variations therein without departing from the scope of the invention.

What is claimed is:

1. A biopsy device having a removable handle for alternatively attaching and removing a handle assembly while a cannula portion of the device is inserted into a patient, without affecting the orientation of the cannula portion within said patient, said biopsy device comprising:

an outer cannula having a proximal end, a distal end, and a substantially hollow cross-section between said proximal and distal ends;

an inner rod capable of being telescopically inserted into and retracted from said outer cannula, said inner rod having a proximal end and a distal end;

a sheath operably associated with said outer cannula, said sheath comprising a locking element, and said sheath surrounding at least a portion of said outer cannula;

a handle assembly removably attachable to said sheath, said handle assembly comprising a locking element and an opening for receiving at least a portion of said sheath, whereby said sheath may be at least partially inserted within said handle assembly and attached thereto, thereby retainably, yet releasably, locking said handle assembly to said outer cannula and said inner rod; and a release member for releasing said handle assembly from attachment to said sheath and, in turn, to said outer cannula and said inner rod, by interacting with said locking elements associated with said sheath and said handle assembly;

said release member comprising a release element capable of being repositioned by the user between at least two positions in order to alternatively lock and release said handle assembly to said sheath;

said release member further being maintainable at each of said at least two positions without further positioning by the user.

2. The biopsy device according to claim 1, in which said locking element associated with said sheath comprises at least one slot on said sheath, said at least one slot capable of interacting with at least a portion of said release member so as to prevent separation of said sheath and said handle assembly.

3. The biopsy device according to claim 2, in which said locking element associated with said handle assembly comprises at least one aperture in said handle assembly, said at least one aperture capable of interacting with at least a portion of said release member so as to prevent separation of said sheath and said handle assembly.

4. The biopsy device according to claim 3, in which said release member comprises a rotatable collar associated with at least one of said sheath and said handle assembly, said rotatable collar capable of being rotated at least partially about said sheath and said handle assembly when said sheath and said handle assembly are joined together, said rotatable collar having at least two stationary positions, so that when said rotatable collar is in one of said positions, a portion of said rotatable collar interacts with both of said locking elements associated with said sheath and said handle assembly to prevent separation of said sheath and said handle assembly, said rotatable collar in the other of said stationary positions avoiding interaction with both of said locking elements, thereby permitting separation of said sheath and said handle assembly for release therebetween.

5. The biopsy device according to claim 3, in which said release member comprises a slide member associated with at least one of said sheath and said handle assembly, said slide member being capable of lateral movement relative to said sheath and said handle assembly when said sheath and said handle assembly are joined together, said slide member having at least two stationary positions, so that when said slide member is in one of said positions, a portion of said slide member interacts with both of said locking elements associated with said sheath and said handle assembly to prevent separation of said sheath and said handle assembly, said slide member in the other of said stationary positions avoiding interaction with both of said locking elements, thereby permitting separation of said sheath and said handle assembly for release therebetween.

6. The biopsy device according to claim 1, in which said opening in said handle assembly for receipt of said sheath is asymmetrical about at least one axis substantially perpendicular to the longitudinal axis of said opening in said handle assembly.

7. The biopsy device according to claim 6, wherein at least a portion of said sheath has an asymmetrical cross-section substantially similar to that of said asymmetrical opening in said handle assembly, so as to be insertable into said handle assembly only when said sheath and said handle assembly are aligned in one particular orientation, thereby ensuring that said outer cannula and said inner rod are aligned in said one particular orientation relative to said handle assembly when said sheath and said handle assembly are locked together.

8. The biopsy device according to claim 1, in which at least a portion of the outer surface of said sheath is threaded to enable the attachment of a comparably threaded component of a separate conduit for attachment to said outer cannula after removal of said handle assembly from said sheath.

9. The biopsy device according to claim 1, further including an attachment member for securably attaching said inner rod within said outer cannula.

10. The biopsy device according to claim 9, in which said attachment member comprises at least one prong associated with said inner rod for engaging with said sheath to securably attach said inner rod within said outer cannula.

11. The biopsy device according to claim 1, further including a locking indicia for readily indicating whether said sheath and said handle assembly are in a locked or an unlocked orientation, relative to one another.

12. The biopsy device according to claim 1, wherein said inner rod comprises at least one of an inner cannula, a stylet, an obturator and an ejector rod.

13. A biopsy device having a removable handle for alternatively attaching and removing a handle assembly while a cannula portion of the device is inserted into a patient, without affecting the orientation of the cannula portion within said patient, said biopsy device comprising:
an outer cannula having a proximal end, a distal end, and a substantially hollow cross-section between said proximal and distal ends;
an inner rod capable of being telescopically inserted into and retracted from said outer cannula, said inner rod having a proximal end and a distal end;
a sheath operably associated with said outer cannula, said sheath comprising a locking element, and said sheath surrounding at least a portion of said outer cannula;
a handle assembly removably attachable to said sheath, said handle assembly comprising a locking element and an opening for receiving at least a portion of said sheath, whereby said sheath may be at least partially inserted within said handle assembly and attached thereto, thereby retainably, yet releasably, locking said handle assembly to said outer cannula and said inner rod;
a release member for releasing said handle assembly from attachment to said sheath and, in turn, to said outer cannula and said inner rod, by interacting with said locking elements associated with said sheath and said handle assembly; and
wherein said release member is a release element capable of toggling by the user between at least two positions in order to alternatively lock and release said handle assembly to said sheath.

14. A biopsy device having a removable handle for alternatively attaching and removing a handle assembly while a cannula portion of the device is inserted into a patient, without affecting the orientation of the cannula portion within said patient, said biopsy device comprising:
an outer cannula having a proximal end, a distal end, and a substantially hollow cross-section between said proximal and distal ends;
an inner rod capable of being telescopically inserted into and retracted from said outer cannula, said inner rod having a proximal end and a distal end;
a sheath operably associated with said outer cannula, said sheath comprising a locking element, and said sheath surrounding at least a portion of said outer cannula;
a handle assembly removably attachable to said sheath, said handle assembly comprising a locking element and an opening for receiving at least a portion of said sheath, whereby said sheath may be at least partially inserted within said handle assembly and attached thereto, thereby retainably, yet releasably, locking said handle assembly to said outer cannula and said inner rod;
a release member for releasing said handle assembly from attachment to said sheath and, in turn, to said outer cannula and said inner rod, by interacting with said locking elements associated with said sheath and said handle assembly; and
wherein at least a portion of the outer surface of said sheath is threaded to enable the attachment of a comparably threaded component of a separate conduit for attachment to said outer cannula after removal of said handle assembly from said sheath.

15. A biopsy device having a removable handle for alternatively attaching and removing a handle assembly while a cannula portion of the device is inserted into a patient, without affecting the orientation of the cannula portion within said patient, said biopsy device comprising:
an outer cannula having a proximal end, a distal end, and a substantially hollow cross-section between said proximal and distal ends;
an inner rod capable of being telescopically inserted into and retracted from said outer cannula, said inner rod having a proximal end and a distal end;
a sheath operably associated with said outer cannula, said sheath comprising a locking element, and said sheath surrounding at least a portion of said outer cannula;
a handle assembly removably attachable to said sheath, said handle assembly comprising a locking element and an opening for receiving at least a portion of said sheath, whereby said sheath may be at least partially inserted within said handle assembly and attached thereto, thereby retainably, yet releasably, locking said handle assembly to said outer cannula and said inner rod;
a release member for releasing said handle assembly from attachment to said sheath and, in turn, to said outer cannula and said inner rod, by interacting with said locking elements associated with said sheath and said handle assembly;
an attachment member for securably attaching said inner rod within said outer cannula; and
wherein said attachment member comprises at least one prong associated with said inner rod for engaging with said sheath to securably attach said inner rod within said outer cannula.

* * * * *